US009074985B2

(12) United States Patent
Lebental et al.

(10) Patent No.: US 9,074,985 B2
(45) Date of Patent: Jul. 7, 2015

(54) METHOD AND DEVICE FOR ACOUSTIC ANALYSIS OF MICROPOROSITIES IN A MATERIAL SUCH AS CONCRETE USING MULTIPLE CMUTS TRANSDUCERS INCORPORATED IN THE MATERIAL

(75) Inventors: Berengere Lebental, Levallois Perret (FR); Elisabeth Delevoye, Grenoble (FR); Anne Ghis, Saint Martin d'heres (FR)

(73) Assignees: COMMISSARIAT A L'ENERGIE ATOMIQUE ET AUX ENERGIES ALTERNATIVES, Paris (FR); LABORATOIRE CENTRAL DES PONTS ET CHAUSSEES, Paris (FR); ECOLE NATIONALE DES PONTS ET CHAUSSEES, Marne la Vallee (FR)

( * ) Notice: Subject to any disclaimer, the term of this patent is extended or adjusted under 35 U.S.C. 154(b) by 1022 days.

(21) Appl. No.: 13/130,492
(22) PCT Filed: Nov. 20, 2009
(86) PCT No.: PCT/EP2009/065580
§ 371 (c)(1), (2), (4) Date: May 20, 2011
(87) PCT Pub. No.: WO2010/057990
PCT Pub. Date: May 27, 2010

(65) Prior Publication Data
US 2011/0226065 A1    Sep. 22, 2011

(30) Foreign Application Priority Data
Nov. 21, 2008 (FR) .................................. 08 57927

(51) Int. Cl.
G01N 29/32    (2006.01)
G01N 29/04    (2006.01)
(Continued)

(52) U.S. Cl.
CPC ............ *G01N 29/045* (2013.01); *G01N 15/088* (2013.01); *G01N 29/2406* (2013.01);
(Continued)

(58) Field of Classification Search
CPC ............. G01N 15/088; G01N 29/045; G01N 29/2406; G01N 29/2475; G01N 29/2481; G01N 2291/044; G01N 2291/02408; G01N 2291/02416; G01N 2291/0245; G01N 2291/0251; G01N 2291/0289; G01N 2291/0232
USPC ..................................... 73/627, 632
See application file for complete search history.

(56) References Cited

U.S. PATENT DOCUMENTS 4,262,399 A * 4/1981 Cady ............................... 438/53
4,432,007 A * 2/1984 Cady ............................. 257/417
(Continued)

FOREIGN PATENT DOCUMENTS

GB    2 293 653 A    4/1996
GB    2293653 A  *  4/1996    ............. G01N 15/08
(Continued)

OTHER PUBLICATIONS

Punurai et al. ("Characterization of multi-scale porosity in cement paste by advanced ultrasonic techniques," Cement and Concrete Research, pp. 38-46, Sep. 20, 2006, School of Civil and Environmental Engineering, Georgia Institute of Technology, Atlanta, GA 30332, United States hereinafter referred to as "Punurai").*

(Continued)

*Primary Examiner* — Laura Martin
*Assistant Examiner* — Samir M Shah
(74) *Attorney, Agent, or Firm* — Oblon, McClelland, Maier & Neustadt, L.L.P.

(57) ABSTRACT

The invention concerns a device for analysing the microporosities of a given material including at least two phases, one of which is a fluid phase, including: multiple sensors (100) incorporated in the given material (M), where each of the sensors includes one or more cMUT acoustic and capacitive transducers.

15 Claims, 7 Drawing Sheets

(51) Int. Cl.
*G01N 15/08* (2006.01)
*G01N 29/24* (2006.01)

(52) U.S. Cl.
CPC ........ *G01N29/2475* (2013.01); *G01N 29/2481* (2013.01); *G01N 2291/0232* (2013.01); *G01N 2291/02408* (2013.01); *G01N 2291/02416* (2013.01); *G01N 2291/0245* (2013.01); *G01N 2291/0251* (2013.01); *G01N 2291/0289* (2013.01); *G01N 2291/044* (2013.01)

(56) References Cited

U.S. PATENT DOCUMENTS

| | | | |
|---|---|---|---|
| 5,619,476 A * | 4/1997 | Haller et al. | 367/181 |
| 5,870,351 A * | 2/1999 | Ladabaum et al. | 367/163 |
| 5,894,452 A * | 4/1999 | Ladabaum et al. | 367/163 |
| 6,262,946 B1 * | 7/2001 | Khuri-Yakub et al. | 367/181 |
| 6,381,197 B1 * | 4/2002 | Savord et al. | 367/178 |
| 6,690,182 B2 | 2/2004 | Kelly et al. | |
| 6,829,131 B1 * | 12/2004 | Loeb et al. | 361/234 |
| 6,913,384 B2 | 7/2005 | Park et al. | |
| 7,023,065 B2 * | 4/2006 | Ayazi et al. | 257/414 |
| 7,274,623 B2 * | 9/2007 | Bayram et al. | 367/140 |
| 7,404,325 B2 * | 7/2008 | Delevoye | 73/504.13 |
| 7,477,572 B2 * | 1/2009 | Caronti et al. | 367/140 |
| 7,800,189 B2 * | 9/2010 | Caliano et al. | 257/419 |
| 7,901,358 B2 * | 3/2011 | Mehi et al. | 600/447 |
| 8,014,231 B2 * | 9/2011 | Oliver et al. | 367/140 |
| 8,406,084 B2 * | 3/2013 | Buccafusca et al. | 367/176 |
| 8,531,919 B2 * | 9/2013 | Cheng et al. | 367/181 |
| 8,767,512 B2 * | 7/2014 | Hajati | 367/140 |
| 2001/0035700 A1 * | 11/2001 | Percin et al. | 310/324 |
| 2005/0018536 A1 * | 1/2005 | Caliano et al. | 367/7 |
| 2005/0148899 A1 * | 7/2005 | Walker et al. | 600/553 |
| 2005/0150692 A1 * | 7/2005 | Ballantyne et al. | 175/61 |
| 2006/0007045 A1 * | 1/2006 | Fiasca et al. | 343/700 MS |
| 2007/0046479 A1 | 3/2007 | Hines | |
| 2007/0059858 A1 * | 3/2007 | Caronti et al. | 438/50 |
| 2007/0287918 A1 | 12/2007 | Huang | |
| 2008/0179993 A1 * | 7/2008 | Sanderson | 310/319 |
| 2008/0184549 A1 * | 8/2008 | Nguyen-Dinh et al. | 29/594 |
| 2008/0212407 A1 * | 9/2008 | Caliano et al. | 367/140 |
| 2008/0309195 A1 | 12/2008 | Sanderson | |
| 2009/0048522 A1 | 2/2009 | Huang | |
| 2009/0152980 A1 | 6/2009 | Huang | |
| 2009/0251025 A1 * | 10/2009 | Kondou et al. | 310/316.01 |

FOREIGN PATENT DOCUMENTS

| | | |
|---|---|---|
| JP | 56-3455 | 6/1979 |
| JP | 2006-157320 A | 6/2006 |
| WO | WO 2004/046704 A1 | 6/2004 |
| WO | WO 2006/132965 A2 | 12/2006 |
| WO | WO 2007/025172 A2 | 3/2007 |
| WO | WO 2007/030423 A2 | 3/2007 |
| WO | WO 2007/030423 A3 | 3/2007 |
| WO | WO 2007/115283 A2 | 10/2007 |

OTHER PUBLICATIONS

Ergun et al. ("Capacitive Micromachined Ultrasonic Transducers: Theory and Technology," pp. 76-84, Journal of erospace Engineering ASCE, Apr. 2003 hereinafter referred to as "Ergun").*

English Translation of Toshiaki (JP 2006-157320).*
U.S. Appl. No. 13/130,397, filed May 20, 2011, Lebental et al.
French Preliminary Search Report issued Jul. 15, 2009, in Patent Application No. 0857927.
Jie Zhang et al., "Hydration monitoring of cement-based materials with resistivity and ultrasonic methods" Materials and Structures/ Materiaux et Constructions, Jan. 2009 Springer Science and Business Media Netherlands NL, vol. 42, No. 1, XP002534795, Mar. 12, 2008, pp. 15-24.
Bérengère Lebental et al. "In-situ non-destructive testing of cementitous materials via embedded ultrasonic transducers made up of carbon nanotubes", 7th International Symposium on Non Destructive Testing in Civil Engineering, XP002571705, Jul. 3, 2009, pp. 1-6.
D.M. McCann et al., "Review of NDT methods in the assessment of concrete and masonry structures", NDT&E International, vol. 34, 2001, pp. 71-84.
W. P. Eaton et al., "Micromachined pressure sensors: review and recent developments", Smart Mater. Struct., vol. 6, 1997, pp. 530-539.
Shuyun Wu et al., "MEMS flow sensors for nano-fluidic applications", Sensors and Actuators A, vol. 89, No. 1-2, Mar. 2001, pp. 152-158.
Chia-Yen Lee et al., "MEMS based Humidity Sensors with Integrated Temperature Sensors for Signal Drift Compensation", Sensors, 2003. Proc. of IEEE, Oct. 2003, vol. 1, pp. 384-388.
Chia-Yen Lee et al., "Micromachine-based humidity sensors with integrated temperature sensors for signal drift compensation", J. Micromech. Microeng., vol. 13, 2003, pp. 620-627.
Isabelle Etchart et al., "MEMS sensors for density-viscosity sensing in a low-flow microfluidic environment", Sensors and Actuators A: Physical A, vol. 141 , Feb. 2008, pp. 266-275.
E. Hernández-Baltazar et al., "Surface properties of an associative alkali soluble polymer(Acrysol TT-935)", Colloids and Surfaces A: Physicochemical and Engineering Aspects, vol. 238, Issues 1-3, May 4, 2004, pp. 113-122.
Hiroshi Ban et al., "Synthesis of alkali-soluble silicone resin suitable for resist material in microlithography", Polymer, vol. 31, Issue 3, Mar. 1990, pp. 564-568.
Lung-Jieh Yang et al., "Photo-patternable gelatin as protection layers in low-temperature surface micromachinings", Sensors and Actuators A: Physical, vol. 103, Jan. 2003, pp. 284-290.
Charles Hautamaki et al., "Experimental Evaluation of MEMS Strain Sensors Embedded in Composites", Journal of MicroElectromechanical Systems, vol. 8, No. 3, Sep. 1999, pp. 272-279.
B. T. Khuri-Yakub et al., "The Capacitive Micromachined Ultrasonic Transducer (CMUT) as a Chem/Bio Sensor", 2007, IEEE Ultrasonics Symposium, pp. 472-475.
K. K. Park et al., "Capacitive micromachined ultrasonic transducers for chemical detection in nitrogen", Applied Physics Letters, vol. 91;094102, 2007, 3 pages.
Japanese Office Action issued Nov. 12, 2013 in Patent Application No. 2011-536879.
U.S. Appl. No. 14/324,379, filed Jul. 7, 2014, Le Prado, et al.

* cited by examiner

METHOD AND DEVICE FOR ACOUSTIC ANALYSIS OF MICROPOROSITIES IN A MATERIAL SUCH AS CONCRETE USING MULTIPLE CMUTS TRANSDUCERS INCORPORATED IN THE MATERIAL

TECHNICAL FIELD

The present invention concerns the field of detection and analysis of microporosities in materials having several phases, including at least one first solid phase and at least one second liquid or gaseous phase, in particular the cement materials such as concrete.

It provides an improved system for detection and analysis of microporosities, and in particular of the capillary porosities of a material with several phases, including at least one fluid phase, using multiple emitters and receivers of acoustic waves incorporated in the material to be analysed.

The invention has applications, for example, such as the analysis of cement materials.

STATE OF THE PRIOR ART

Cement materials are biphasic materials formed from a fluid phase and a solid phase. The fluid phase is generally called "porosity".

The pores may have a characteristic dimension which may be of the order of several tens of angstroms to several centimetres.

Pores of the size of the order of a micron, also called "microporosities", play an essential role in the macroscopic properties of the cement materials.

Depending on the size of the pores it is possible to distinguish several classes of porosities:

1. capillary pores, of very irregular shape, and of a size generally between 10 nm and 10 μm,
2. pores called "hollow-shell" (or also called "Hadley grain") of large size and of simple geometric shapes (such as a triangle, an ovoid shape, etc.), which are surrounded by a ring with a base of C—S—H, and which result from a hydration mechanism which leaves a partially or completely empty shell,
3. pores included in cement paste of low density, called "open-gel", of a size of between 0.5 nm and 10 nm,
4. pores included in dense cement paste, called "dense-gel", of a diameter smaller than 0.5 nm.

The $3^{rd}$ and $4^{th}$ classes form a porosity called "nano-porosity".

An analysis of the porosity of classes 1 and 2 is particularly useful.

In cement materials the porosity may be an indicator of harmful reactions, such as alkali reactions or carbonation, and can, for example, constitute an indicator of a possible corrosion of the armatures of the concrete.

The porosity influences the process of hydration of the cement materials and their mechanical properties. An analysis of the porous structure may enable the properties of the materials to be improved, either during the lifetime of a studied structure, for example by modifying curing parameters, or with the aim of developing new methods or new products.

From a study of the porosity of a material it is possible to deduce its macroscopic transport parameters, such as permeability, or the ion diffusion coefficient.

The transport parameters are significant in the definition of the durability of the material in question, particularly when this material is in a wet medium, as is the case with cement materials.

There are many techniques for analysing the porosity of cement materials.

Porosimetry by mercury intrusion is, for example, a technique in which mercury is injected into a cement paste under increasing pressure. By measuring the volume introduced it is possible to deduce the size distribution of the pores in this paste, for example by using a law known as "Washburn's law".

This technique has many limitations: the samples to be studied are previously dried in order to empty the pores, which can modify their structure. In addition, the high pressures applied to the mercury can lead to local fractures of the material, and make the porosity coarser. The hypotheses for validity of the method (shape of pores and accessibility) are not systematically met, which introduces a systematic error in relation to the entire porous volume: rather than being associated with a pore size, each portion of volume introduced is associated with the widest opening giving access to such pores.

Imaging can also be used in order to study the porosity of a material. The most common method is scanning electron microscopy. Such a method generally requires a complex preparation of samples of the material.

In order to be analysed the sample is cut up and polished in order to provide a flat surface. It must usually also be dried, which may modify the structure of the material. In addition, the imaging data obtained is in two dimensions.

RMN imaging, for its part, enables an image in three dimensions to be provided. This technique is based on the use of gradients of magnetic fields. The resolution of this technique is currently insufficient.

An analysis by adsorption of gas can also be used to study the porosity of a material.

Such a method is based on the fact that the condensation of the gas is modified when this gas is included in pores, compared to when this gas is free. This difference is due to the interactions of the gas molecules with the atoms of the surface of the solid. The measurement of the volume of gas ($N_2$, $H_2O$, etc.) adsorbed on the walls of the pores as a function of the applied pressure enables isotherms to be plotted. Using hypotheses such as, notably, the number of layers adsorbed, it is possible to evaluate the surface specific area of the porous material, i.e. the area per unit of mass.

This technique enables the micro- and nano-porosity, also called the "fine porosity", down to a few angstroms, to be analysed. However, it requires a prior step of drying, which may be very long, and which may modify the structure of the material. In addition, the results obtained depend partly on the conditions of preparation of the material.

A method called "diffusion at small angles" consists, for its part, in analysing the intensity of a radiation diffused by the material. Diffusion techniques at small angles generally use a neutron radiation or X-ray radiation. The diffusion figure gives statistical information on all the diffusing objects. This technique is non-destructive and requires no drying step. The spectrum of their various resolutions is broad.

However, preparation of the samples requires substantial pretreatment, which is likely to interfere with the results. Most of the methods based on this technique are destructive.

In addition to these high-resolution but destructive evaluation methods there are evaluation methods which do not destroy the structures. These methods, which are undertaken in situ, are for example radar methods or methods using acoustic waves.

An example of such a method is given in the document: Review of Non Destructive Testing Methods in the assessment of concrete and masonry structures, D. M. McCann, M. C. Forde in NDT&E International 34 (2001) 71-84).

With regard to the acoustic methods, there are impact methods, vibratory methods and ultrasonic methods.

Generally, these methods do not exceed an operating frequency of 20 KHz, which limits their resolution to some ten cm.

Acoustic methods operating at frequencies of the order of 1 MHz, i.e. a resolution of the order of 3 mm, are presented in the document "methods for multiple scattering of ultrasounds in random media", M. Chekroun et al. Numerical, but they are limited to the analysis of macroscopic structures due to their resolution.

The study of microporosity in cement materials is determining. Monitoring of the microstructure of such materials is an indicator of the capacity of these materials to fulfil their function, and is a condition for their durability.

As has been indicated, there is a broad range of investigative techniques to understand the microporosity.

The problem of finding a new method of analysis of the porosity of the cement materials which does not have the disadvantages mentioned above is thus posed.

ACCOUNT OF THE INVENTION

The invention firstly concerns a device for analysing porosity, and more specifically the micro-porosity, of a given material having at least two phases, including at least one fluid phase, including: multiple sensors incorporated in said given material, where each of the sensors include one or more cMUT-type capacitive electroacoustic transducers (cMUT for "Capacitive Micromachined Ultrasonic Transducers").

The device of the invention enables the microporosity, and particularly capillary porosity, to be monitored, without the microporosities being distributed uniformly in the material.

The sensors can have one or more sensitive zones of a critical dimension of between 1 nm and 100 µm.

The sensors can have sensitive zones the length and width of each of which are smaller than 100 µm.

Sensors with sensitive zones having such dimensions enable measurements to be made in small volumes corresponding to microporosities.

"Sensitive zones" is taken to mean zones or elements intended to vibrate, in order to emit and/or receive acoustic waves.

"Critical dimension" is taken to mean the smaller dimension of these sensitive zones, excluding their thickness.

Sensitive zones of such dimensions enable the sensors to excite the microporosities acoustically, in an individual manner.

The transducers can be cMUTs transducers of a capacitive type.

An analysis of the microporosities, i.e. of pores of diameter smaller than 100 µm can be made using such a device.

It is thus possible to undertake an analysis of the pores of the size of the order of a micron of a material, by emitting acoustic waves in this material, and by analysing acoustic waves resulting from this emission through cMUTS receivers incorporated in the material.

Each sensor thus includes at least one cMUT transducer receiving acoustic waves. The device may also include: multiple cMUTs emitting transducers incorporated in said given material.

The cMUTS transducers incorporated in the material to be analysed can be transducers operating as acoustic wave emitters, as acoustic wave receivers or as emitter-receivers.

According to one possibility, the cMUTs can have at least one membrane including at least one layer with a base of nanotubes and/or nanowires and/or nanorods, where the membrane is intended to generate and/or detect acoustic waves.

This can enable a device to be implemented with a membrane responding both to a criterion of small dimensions in terms of area and thickness, and an operational criterion, since it operates at high frequency.

Emitting transducers can be designed to emit acoustic pulses in a range of frequencies of between 20 kHz and 100 GHz, and in particular between 100 MHz and 10 GHz.

Such a range is suitable in particular for the analysis of microporosities or pores of the size of the order of one nanometre to some ten microns.

The transducers can include one or more membranes intended to oscillate under the effect of an electric field and/or an acoustic wave, where the membrane or membranes are formed from one or more layers of nanotubes and/or nanowires and/or nanorods.

The device can also include multiple supports of the sensors incorporated in said given material, where each of the sensors lies on a support including at least one electronic circuit for processing signals produced by at least one sensor.

Such a circuit may include, for example, at least one amplification stage or module.

Such a circuit may possibly include, for example, at least one filtering stage or module.

The supports of the sensors may each include a matrix of cMUTS transducers and/or several sensors of different types, including at least one cMUT transducer.

According to a possible implementation, the sensors may include an integrated power supply and/or be powered through a source of electrical power external to said material.

According to a possible implementation the sensors may include means to emit signals to outside the material, where the device also includes a data-processing device which is external to the material, and which is connected to the sensors through RF and/or wired connections.

According to a possible implementation the sensors may covered with a protective casing.

According to one possibility, the sensors may be protected by a protective casing formed from at least one permanent protective layer, based on a material which is stable in a basic or acid medium.

The permanent protective layer may partially cover the sensors such that the sensitive zone, at least, is not covered by the permanent protective layer.

A protective casing formed from a first permanent protective layer, and from a second temporary protective layer, and having a base of a second material, for example a material likely to be damaged after the incorporation of the sensor into the material to be studied, may be used.

The protective casing may be designed such that the sensitive zone or zones of the sensors, i.e. the zone or zones intended to emit and/or receive acoustic waves, for example one or more membranes, are covered only by the second protective layer, such that the sensitive zone or zones are thus directly in contact with the material to be studied after the deterioration of the second protective layer.

The invention also concerns a method for analysing the porosity, and more specifically the microporosity, of a given material having at least two phases, including the steps:

of emission by one or more cMUTS capacitive acoustic transducers, the transducers being incorporated in said given material, of at least one given acoustic wave, reception by at least one cMUT capacitive acoustic transducer, the transducer being incorporated in said given material, of at least one wave resulting from the emission of said given acoustic wave.

An analysis of the microporosities, i.e. of pores of diameter smaller than 100 μm, can be made.

Prior to the measurement the sensors can be distributed at random in said given material when the latter is in an at least partially liquid state, the measurement being made after at least partial solidification of said given material.

During this distribution, one or more sensors may be protected by a protective casing formed from at least one permanent protective layer, where said protective casing is formed from at least one temporary protective layer, intended gradually to deteriorate after the incorporation in said given material.

BRIEF DESCRIPTION OF THE ILLUSTRATIONS

The present invention will be better understood on reading the description of examples of embodiment given, purely as an indication and in no way limiting, making reference to the annexed illustrations in which.

Identical, similar or equivalent parts of the various figures have the same numerical references, to make it easier to go from one figure to another.

The various parts represented in the figures are not necessarily represented with a uniform scale, in order to make the figures more readable.

DETAILED ACCOUNT OF PARTICULAR EMBODIMENTS

Figure 1:
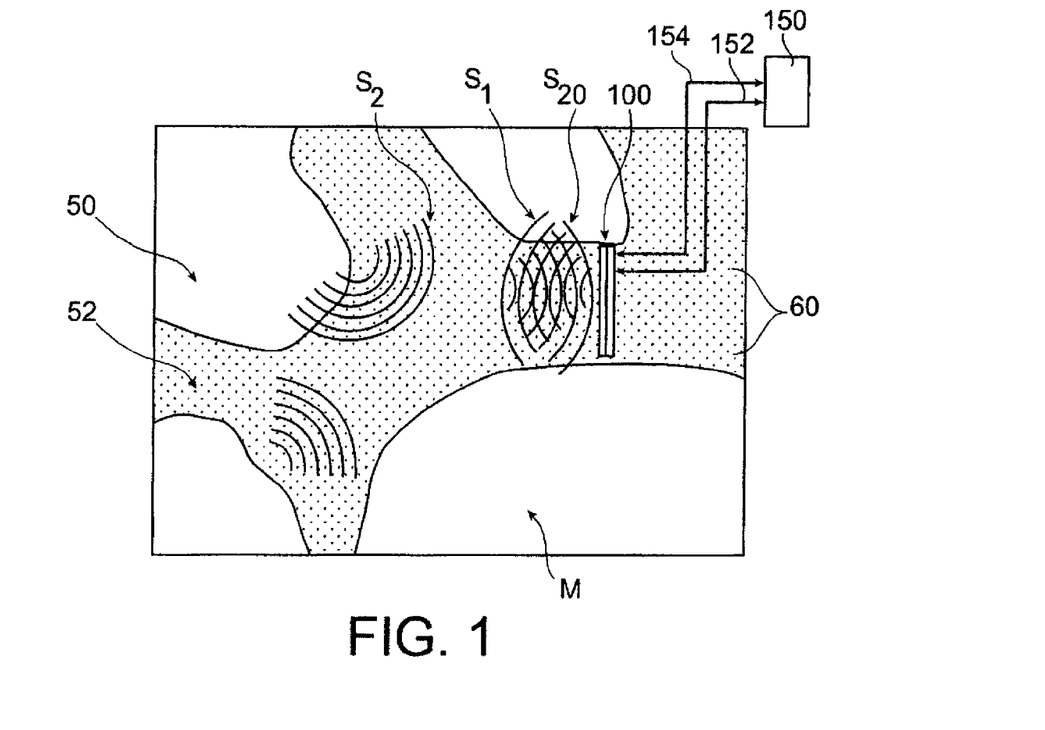
FIG. 1 gives an example of an MEMS sensor encapsulated in a cement material, and belonging to a device for analysing the microporosity of said material.

An example of a device for analysing the microporosities of a material with several phases is given in FIG. 1.

The studied material is a biphasic material in which the MEMS (MEMS for "Micro Electro Mechanical Systems") or NEMS (NEMS for "Nano Electro Mechanical Systems") sensors are incorporated, the sensors having been introduced without destroying this material.

The sensors were introduced into the material, for example, when the latter is in a globally liquid form, prior to its solidification. For example, in the case of a cement material, the sensors are distributed at random when this material is in a liquid form, before it solidifies.

The studied material is a biphasic material, or a material with at least two phases, including at least one solid phase and at least one liquid or gaseous phase, at least one fraction of the porosity of which has characteristic dimensions between some ten nanometres and some one hundred microns, and where this porosity can be filled with gas or liquid.

The studied material may be a cement material such as cement or concrete, an asphalt material, a composite construction having at least two phases, or plaster.

In the example of FIG. 1 a portion of cement material including non-hydrated cement grains 50, sites 52 with a base of C—S—H ($CAO$—$SIO_2$—$H_2O$), and microporosities 60 is represented.

This portion of material includes an MEMS (MEMS for "Micro Electro Mechanical Systems") or NEMS (NEMS for "Nano Electro Mechanical Systems") sensor 100 included among several sensors incorporated in said material.

In this example the sensor includes a part which emits acoustic waves S1, or at least one element emitting acoustic waves S1, and a receiving part or at least one element receiving acoustic waves. In this figure certain waves S20 of the waves reflected S2 following the emission of waves S1 by the sensor are represented.

The sensor 100 includes at least one sensitive zone, i.e. one zone or one element intended to vibrate, in order to emit and/or receive acoustic waves. The sensitive zone may be in the form of a membrane.

The sensor 100 may include at least one sensitive zone of dimensions, i.e. of length and width, where each is between 1 nm and 100 μm. Sensors with sensitive zones having such dimensions enable measurements to be made in small volumes corresponding in particular to microporosities. More particularly, using all the measurements supplied by these sensors, it is possible to deduce statistical information concerning the morphology of the microporosity.

The sensor 100 may include, for example, one or more ultrasonic transducers of the capacitive type, commonly called cMUT transducers (cMUT for "Capacitive Micromachined Ultrasonic Transducer"), where the transducer or transducers may act as emitters of acoustic waves, or as receivers of acoustic waves, or as emitter-receivers of acoustic waves.

In the case of a sensor 100 having one or more electroacoustic transducer(s) of the cMUT capacitive type, the active zone is in the form of one or more vibrating membranes.

A large number of microsensors or nano-sensors may have been dispersed in the material to be analysed during the manufacture of the latter, for example a density of between 0.1 and 0.0001 depending on the properties of the sensor and of the material, for example of the order of 0.01. The microsensors on nano-sensors may be dispersed, for example, in cement prior to its solidification.

A statistical analysis of the information derived from the sensors may be made, for example using a data-processing device 150 external to the material, and which is able to communicate with the sensors using at least one wired connection 152 and/or at least one wireless connection 154 (FIG. 1).

The sensors may be queried, for example occasionally or periodically, and the sensors' querying frequency may be modified in the course of their lifetime.

All the sensors may be queried simultaneously, or some only of the sensors may be queried simultaneously, or each sensor may be queried individually.

The sensor may be initialised for example through the emission of an activation signal or "ON" signal, for a given duration, which enables a sensor receiving it to be initialised. Modulated signals may be emitted in the electrode of a cMUT.

A continuous, or periodic or occasional, emission, or an alternation of these modes, may be implemented by each sensor, in order to transmit all or part of the collected information to an external device.

And emission of data may, for example, be controlled by a clock associated with the sensor. An occasional emission may, for example, be made following a change of the sensor's environment having provoked an activation of this sensor, for example when a measured physical magnitude has become higher than a threshold value.

The sensor may detect its environment continuously, or periodically, or occasionally, or according to an alternation of these modes.

A detection action may be activated by the sensor itself or by the external processing device.

The tasks which may be undertaken by the external processing device 150 include a recording operation, an operation to locate the emitting sensor, a spectral analysis operation, an operation to compare with threshold values or to analyse the noise emitted from the sensors, an operation for statistical processing of data originating from the sensors, for example a calculation of an average or a calculation of standard deviation, and an error analysis operation.

Such a processing device may, for example, include a PC computer fitted with a man-machine interface and an acquisition card. In the case of an operating mode in which the external device and the sensors are connected by a wired connection, the PC computer may be connected by a USB or GPIB (bus IEEE 488) or RS232 connector to a card to which connecting wires linked to the sensors are connected.

Sensor 100 may be powered, for example, using a connection, for example a wireless connection, from outside the material, and/or may possibly include an integrated power source.

The sensor 100 may include means for processing the signals received by the cMUT capacitive transducers. Such processing means may, for example, be designed to undertake a spectral analysis of the signal, a comparison with threshold values, or storage/recording operations.

The MEMS/NEMS of the sensor, in particular the sensor's cMUTs transducer or transducers, form(s) an active zone the characteristic dimensions of which define the order of magnitude of the smallest of microporosity dimension observable by the sensor. In the case of an active-zone cMUT sensor of the order of 1 $\mu m^2$, the smallest observable characteristic porosity dimension may be, for example, of the order of 500 nm.

Figure 2:
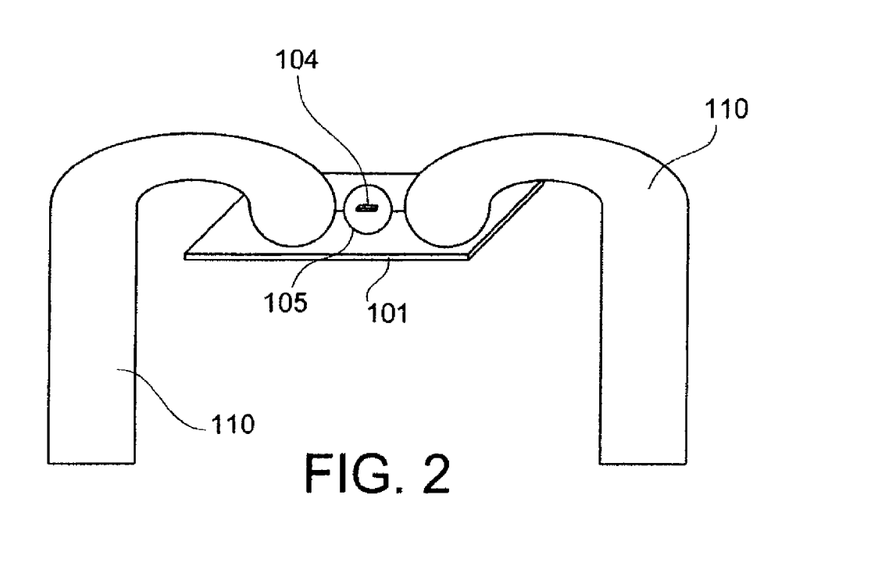
FIG. 2 illustrates an example of a sensor support able to be used within a device for analysing the microporosity of a material.

Active zone 104 (MEMS or NEMS sensor) and its control electronics 105 may be positioned on an identical support 101, for example on a silicon or silicon oxide support, possibly covered by a protective layer, for example a polymer-based layer, and situated at the places where the support is likely to be in contact with the material to be studied.

According to one possibility (FIG. 2), the components situated on the support 101 may possibly be connected to a device external to the material, using gold wires 110. The gold wires 110 can be connected directly to the external device, or can be connected to coaxial cables (not represented) which convey electrical measurement signals outside the material, and which are processed using the electronic processing device 150.

Figure 3A:
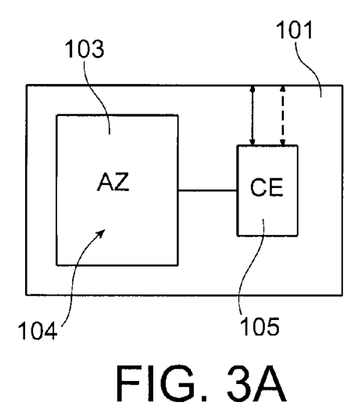
FIGS. 3A-3D illustrate various examples of arrangements of a sensor able to be used within a device according to the invention for analysing the microporosity of a material.

In FIG. 3A the active zone 104 is formed from an acoustic transducer 103 of the cMUT capacitive type in the form of MEMS or NEMS on its support 101.

Figure 3B:
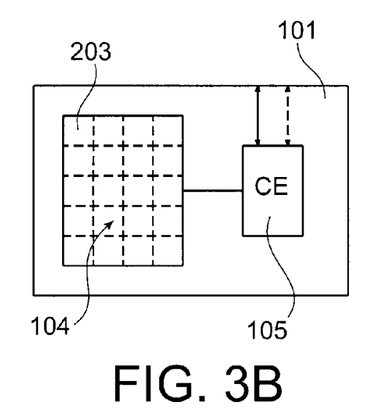

According to a variant the sensors can include an active zone 104 formed from several identical cMUTs transducers 203 distributed on the support 101 and arranged in the form of a matrix of transducers (FIG. 3B).

Figure 3C:
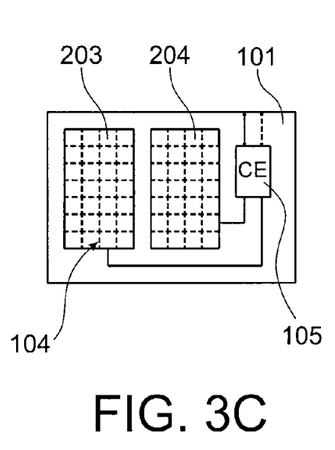

According to another possibility several active zones 104, 204, each formed from a cMUT transducer or a matrix of cMUT transducers 203 can be designed on an identical support 101 (FIG. 3C).

Figure 3D:
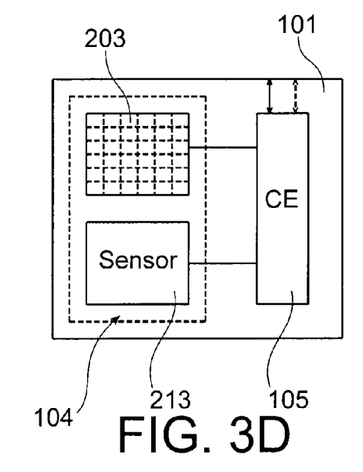

In FIG. 3D several sensors of different types are formed on the same support 101 with, for example, at least one cMUT ultrasonic transducer or a matrix of cMUTs transducers 203, and at least one other sensor 213.

On an identical support 101, a cMUT transducer or a matrix of cMUT transducers may be associated with one or more sensors from among the following sensors: a temperature sensor, a viscosity sensor, a humidity sensor, a pressure sensor.

The sensors incorporated in the cement material such as the sensor 100 described above each include at least one cMUT transducer which can act as an emitter of acoustic waves, or as a receiver of acoustic waves and/or as an emitter-receiver of acoustic waves.

In FIGS. 3A, 3B, 3C, 3D, the support 101 of the transducer or transducers also includes means 105 or a circuit 105 for processing the signals originating from the sensor. This circuit 105 or these means 105 can include means of amplification of signals originating from the transducers, and possibly one or more other signal processing modules, for example a filtering module. This circuit 105 or these means 105 can include means for transmitting signals outside the material, for example at least one RF module.

Figure 4A:
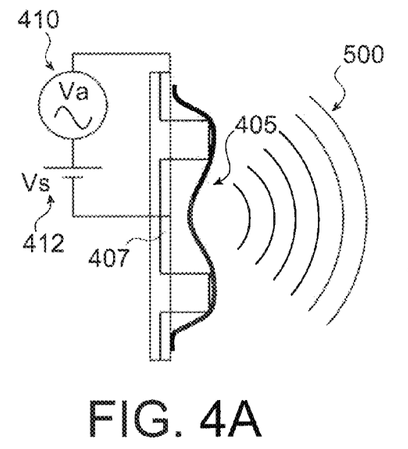
FIGS. 4A, 4B, 4C, 4D illustrate examples of cMUT cells operating respectively as an emitter, or as a receiver, or as an emitter-receiver.

In FIG. 4A a cMUT transducer able to be incorporated in a sensor of a device for analysis of microporosities according to the invention is given. This transducer operates as an acoustic wave emitter 500 and includes a membrane 405 intended to vibrate in a cavity 410 facing an electrode 407. The device is also fitted with means 410 to apply a variable potential Va to the electrode 407, and means 412 to apply a fixed potential Vs to the membrane 405.

Figure 4B:
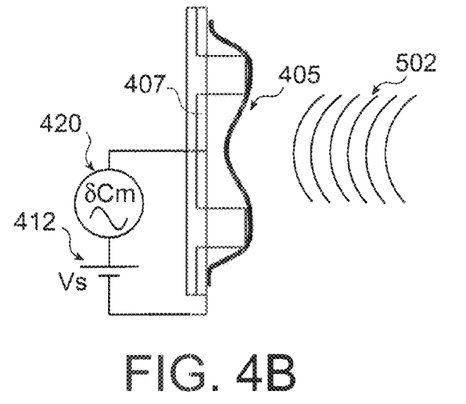

In FIG. 4B a cMUT transducer able to be incorporated in a sensor of a device for analysis of microporosity according to the invention is also represented. The transducer operates as an acoustic wave receiver 502 and includes a membrane 405, and means 412 to apply a fixed potential Vs to the electrode 407, and means 420 forming a capacitance meter, to measure a variation of capacity δCm representative of the waves received by the membrane 405.

Figure 4C:
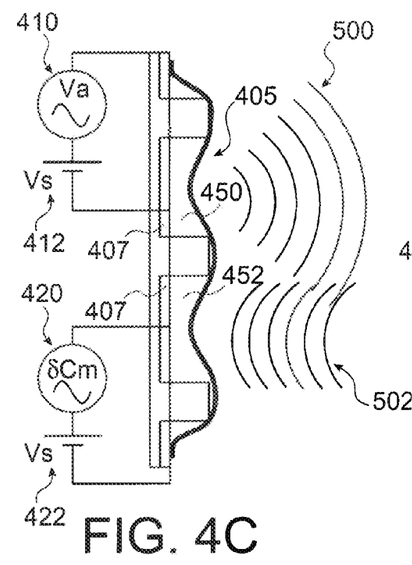

Another example of a cMUT transducer, able to be incorporated in a sensor of the same type as that described above in connection with FIG. 1, is given in FIG. 4C. The transducer operates as an emitter-receiver and includes a membrane 405 suspended above a first cavity 450 and a second cavity 452. The first cavity 450 belongs to the emitting part of the transducer. The cMUT transducer also includes means 410 to apply a variable potential Va to the membrane 405, and means 412 to apply a fixed potential Vs to the electrode 407. The second cavity 452 belongs to the receiving part of the transducer. The transducer also includes means 412 to apply a fixed potential Vs to a second electrode 407, and means 420 to measure a variation of capacity δCm of the membrane 405, connected to the second electrode 407.

Figure 4D:
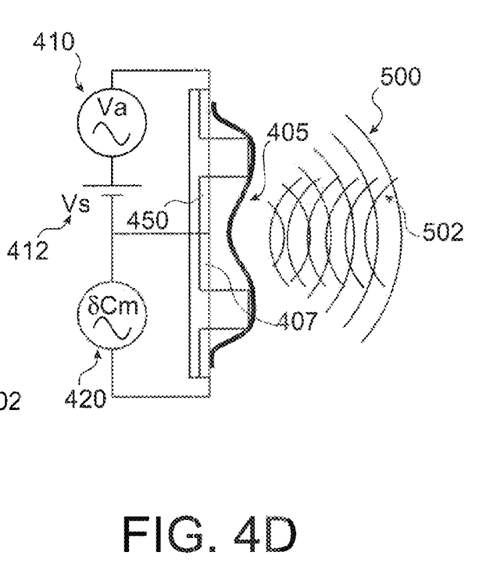

Another example cMUT transducer is given in FIG. 4D. This transducer is able to be incorporated in a sensor of the same type as that described above in connection with FIG. 1, and operates as an emitter-receiver. The transducer includes a membrane 405 and a single cavity 410 such that it can act both as an emitter and as a receiver. The cMUT transducer also includes means 412 to apply a fixed potential Vs to an electrode 407, and means 420 to measure a variation of capacity δCm of the membrane 405, connected to the electrode 107.

The membrane of the transducers which have just been described can be formed from one or more juxtaposed layers of nanotubes (or nanowires or nanorods).

The nanotubes or of nanowires or nanorods have the form of bars of critical dimension between, for example, 0.5 nanometre and 5 microns.

The nanotubes have a tubular shape, whereas the nanowires can have a cylindrical shape, and whereas the nanorods can have a parallelepipedic shape.

The nanotubes or nanowires or nanorods may possibly be associated with one or more "connecting" layers attached to the nanotubes or nanowires, and intended to connect the nanotubes and to be used to provide the sealing of the membrane. Such a connecting layer can, for example, have a graphene base.

Such a membrane can enable a cMUT transducer of very small size to be produced which is capable of operating at high frequencies, compared to the size and frequencies of a habitual transducer. The membrane can, for example, have a width and a length each between 1 nanometre and 100 microns.

Depending on the range of the intended application the active zone of the sensors may be made hydrophilic, for example by functionalisation of a COOH group.

Figure 9:
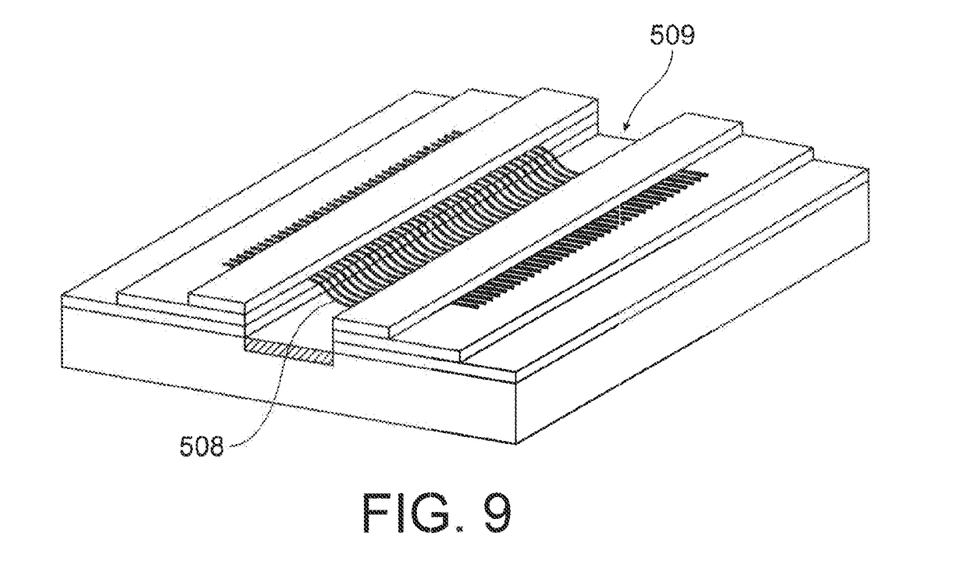
FIG. 9: illustrates an example of a cMUT transducer with an oscillating membrane formed from nanotubes and/or nanowires and/or nanorods.

An example of a cMUT transducer including a membrane 505 formed from juxtaposed nanotubes 508 is given in FIG. 9.

According to a variant, the active zone of the sensors may be made hydrophobic, for example by electropolymerisation with a hydrophobic polymer.

In a case in which the active zone is made hydrophilic or hydrophobic, an identical treatment is applied to the electrodes of the sensor, in particular to the electrode or electrodes situated facing the membrane.

Following the emission of acoustic waves 500, a measurement of the echo return time in the emitter enables a reflecting zone of the waves to be located, and the frequential analysis of these echoes enables the nature of the zones of the material traversed by these waves to be identified.

In order to detect microporosities, i.e. pores of sizes of the order of a micron, the transducers of the device can be designed to emit acoustic pulses in a range of frequencies of between 20 kHz and 50 MHz or between 50 MHz and 100 GHz.

A matrix of emitters or receivers or emitters/receivers as described above, and operated independently by an active matrixing system, based on transistors, can be produced.

Figure 5:
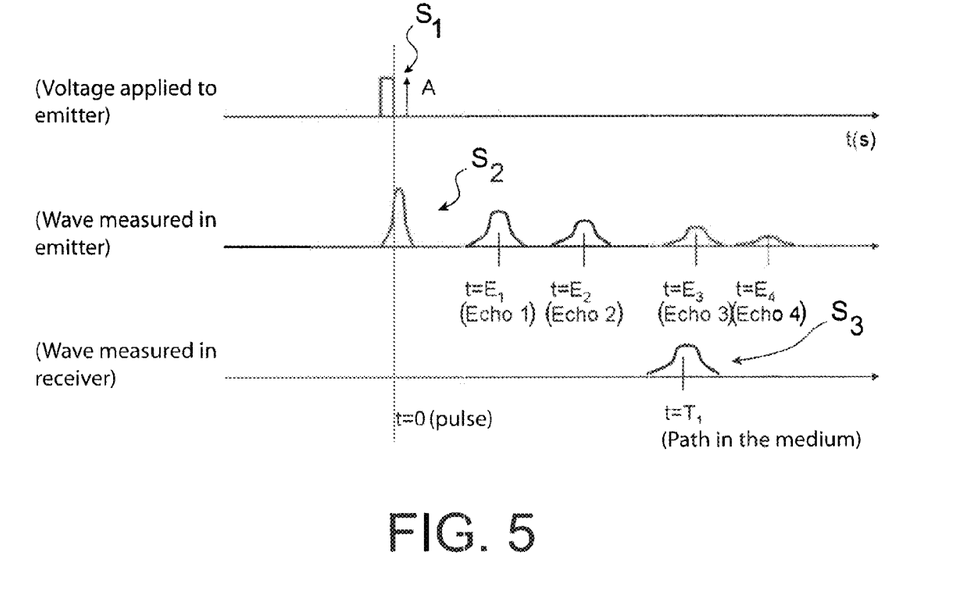
FIG. 5 illustrates an example of pulse operation of a cMUT transducer within a device according to the invention.

The cMUT transducer can have a pulse operating mode (FIG. 5).

In pulse mode, using a voltage pulse (signal S1) applied to the emitter, the emitter can emit in its turn an acoustic wave in the form of a pulse (Signal S2), the temporal spread of which depends on the bandwidth of the emitter and the surrounding medium. For example, when the emitter is located in an aqueous zone of the microporosity, the temporal spread of the signal S2 can be substantial if the medium cuts out high frequencies, whereas in an air zone the temporal spread of the signal S2 is negligible.

For example, depending on the dimension L of the pore opposite the sensor, certain frequencies f ($f=c_{fluid}/L$) of the pulse will also be amplified. Pulse S2 is propagated in the medium and reaches the receiver at distance d after a period $T_1$ ($T_1=d/c_{fluid}$, where $c_{fluid}$ is the speed of sound in the medium). A frequential analysis of a signal S3 received and a comparison of it with emitted signal S2 allows the transfer function of the medium for the frequencies present in the spectrum of the emitter and of the receiver to be determined in a single operation. Pulse S2 can be partially reflected by the medium, leading to successive echoes in the receiver. The time for the echoes to return to the emitter enables the reflecting zone to be located, and the frequential analysis of them enables the nature of the interfaces traversed by pulse S2 to be analysed. The microporosity of the material can thus be analysed.

The return time of each echo can, for example, give an estimate of the distance at which the obstacle which created it is from the emitter. The spectrum can provide information concerning the nature of the obstacle, for example its roughness. The amplitude can provide information concerning the damping factor.

According to a possible implementation of the device, other sensors may be added to the cMUT transducer or to the matrix of cMUT transducers on the support 101. A pressure sensor, for example as described in the document: *Micromachined pressure sensors: review and recent developments* of W. P. Eaton et al, 1997, Smart Mater. Struct. 6 pages 530-539, can, for example, be positioned on the same support 101 as the cMUT transducer.

According to other possibilities a flow sensor of the type as described in the document: *MEMS flow sensors for nanofluidic applications*, by Shuyun Wu, Sensors and Actuators A: Physical Vol 89, No 1-2, March 2001, pages 152-158, or a humidity sensor of the type as described in the document: *MEMS based humidity sensors for signal drift compensation*, by Chia-Yen Lee in Sensors, 2003. Proc. of IEEE, October 2003, Vol 1, pages 384-388 and in *J. Micromech. Microeng.* vol. 13, 2003, pages 620-627, and/or a viscosity sensor as described in the document: *MEMS sensors for density-viscosity sensing in a low flow microfluidic environment*, Isabelle Etchart, Sensors and Actuators A: Physical, Vol 141, No 2, February 2008, pages 266-275, and/or a temperature sensor can be incorporated in the same support 101 as the cMUTS transducer or transducers.

The data recovered by each of the MEMS or NEMS sensors of the device are processed statistically by the device 150 and then fed back to be included in global information concerning the microporosity of the material, for example information concerning the porous volume, the size distribution of the pores, for example information relative to the liquid content (for example water content), a possible saturation with liquid (for example water) of the pores, information concerning the structure of the walls such as, for example, in respect of concrete, the CSH thickness (CSH for $CAO-SiO_2-H_2O$), the CSH density, the roughness or the connectivity of the medium.

The various sensors can give micrometric resolution information concerning the pores and their content, to their immediate surrounds.

The information obtained by a sensor of the device can be local, i.e. concerning solely the region of the material in direct proximity to the active zone of the sensor, with a volume studied by the sensor being the area of the active zone of the sensor multiplied by a small thickness depending on the sensor and the measured parameter, for example between 1 angström and 100 nm.

The information obtained by a sensor of the device can also be remote, i.e. concern a volume V of the microporosity. For example, the resonance frequency of a viscosity sensor depends on the fluid which surrounds it, but also on the fluid domain opposite it.

The sensor 100 is capable of analysing:
a fluid phase, independently of the nearby solid matrix,
a fluid phase in its relationship with a solid phase, for example when the sensor has at least one cMUT transducer used in a pulse mode for which it detects the echoes following signals which it has emitted, in order for example to define a distance between the sensor and a fluid-solid interface.

In the case of a local measurement, magnitudes such as temperature, pressure, humidity or flow in the immediate proximity of the sensor can be measured.

In the case of a remote measurement: an average viscosity measurement of the content of a pore opposite the sensor, a measurement of a porous volume close to the sensor, the content and dimensions of the porosity opposite the sensor, the nature of the fluid-solid interfaces, or the diameters of the inter-pore connecting channels can also be made.

The sensors are distributed at random in the material.

The sensor's environment may take several forms.

Figure 6A:
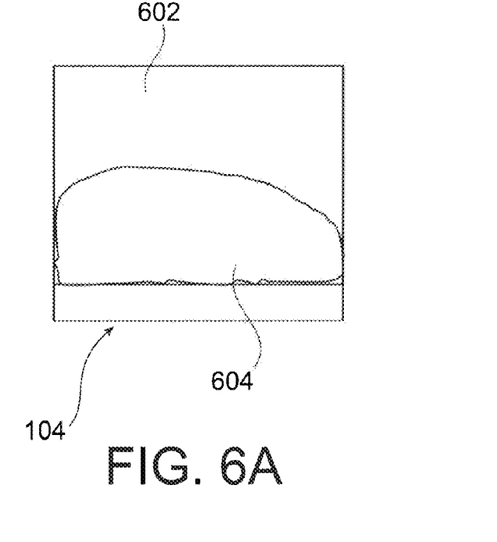
FIGS. 6A-6D show various arrangements of the active zone of a sensor of a device for analysing the microporosity of a material according to the invention.

In FIGS. 6A-6D four possible environments of the sensor are given:

In FIG. 6A the active zone 104 of the sensor is facing the solid phase 604 of the material.

Figure 6B:
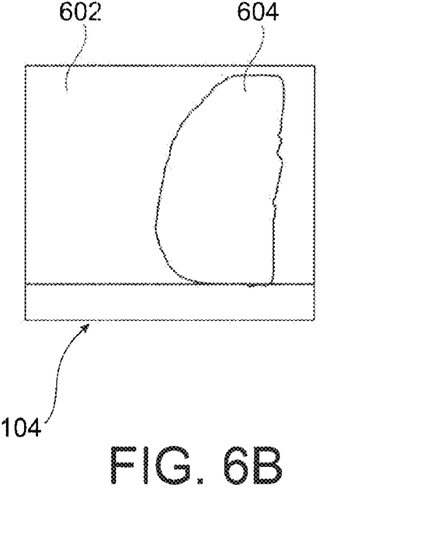

In FIG. 6B the active zone 104 of the sensor is partially facing the solid phase 604, and partially the liquid phase 602.

Figure 6C:
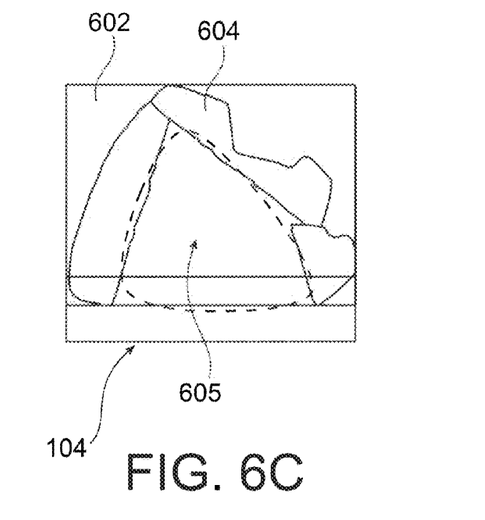

In FIG. 6C, the active zone 104 of the sensor is facing the liquid phase 602 in the form of a closed or unconnected pore 605.

Figure 6D:
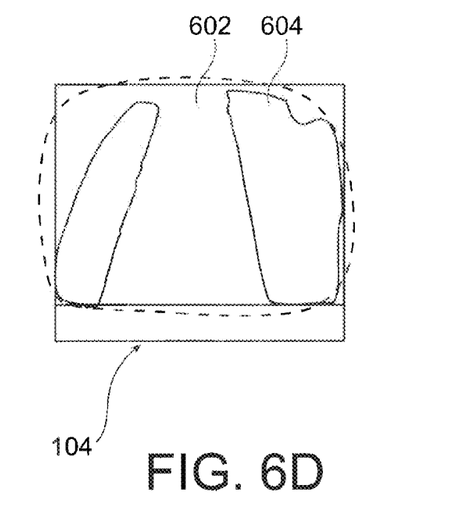

In FIG. 6D, the active zone 104 of the sensor is facing the liquid phase in the form of an open pore 606.

Each sensor is positioned at random in the material, explores a given volume of the porosity and measures at least one parameter in this volume.

If the material in question is uniform all the values measured by all the sensors for this microscopic parameter constitute a sample of this microscopic parameter. It is possible to deduce from them a law of variation of the measured microscopic parameter, and to obtain statistical data such as, for example, an average or a variance.

The number of sensors required may be modified according to the degree of disorder of the material.

If the material is heterogeneous, if an estimate of the scale L is available (with L which may be, for example, the distance between armatures of a bridge and the outside, or for example a distance between armatures in a structure, or for example a distance between two piers of a bridge, or an ion penetration distance in a concrete structure) of variations of the macroscopic properties of the structure of the material, it may be possible to equate the situation to that of a uniform material.

To determine a law of a microscopic parameter at a point M (x,y,z) of the studied material, it is possible to sample this law from the measurements given by sensors located in a ball of radius $r \ll L$ around point M. The accuracy of the estimate of the law of the parameter at point M depends on the number of sensors in the ball of radius r. To obtain the same accuracy as in the case of a homogeneous material the sensor density may be multiplied by $(D/r)^3$, with D being the characteristic dimension of the studied material, and where D designates the scale of homogenisation of the material associated with the measured magnitude.

A choice may be made to maximise r, keeping r such that $r \ll L$.

The method may then be iterated at subsequent instants to monitor the changes in the microstructure.

The invention may possibly apply to other biphasic materials than cement materials, possibly to porous materials: ceramics and polymers.

The microporosity of hydroxyapatite cements used in the medical field to reconstitute bones may, for example, be studied.

Other types of ceramics may also be analysed.

Porous ceramics used, for example, in motor vehicle catalytic converters, porous polymers used, among other contexts, in biomedical materials, and biphasic materials used for thermal insulation, in textiles or in catalytic substrates, can also be analysed using a device and a method according to the invention.

With regard to composite materials, plastic materials such as GFRP (glass reinforced plastic), CFRP (carbon reinforced plastic) or AFRP (aramid fiber reinforced plastic) can also be analysed.

Figure 7:
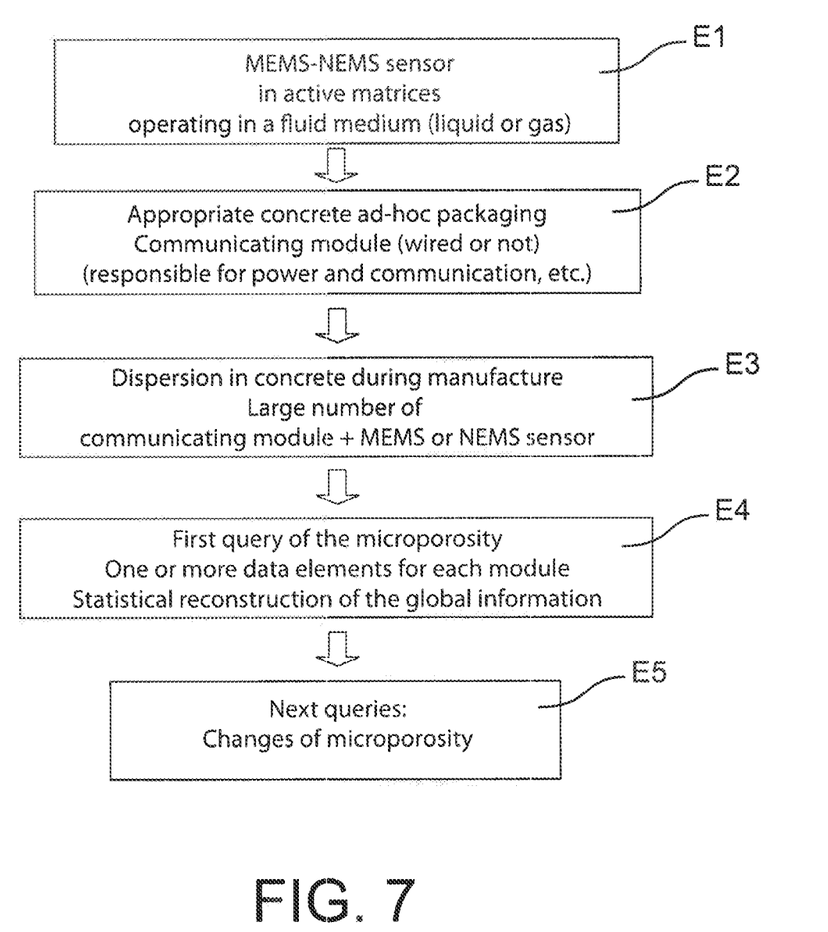
FIG. 7 illustrates in the form of a flow chart the steps of a method for implementation of a device for analysing the microporosity of a cement material.

In FIG. 7, different steps of implementation followed by use of a device for analysing microporosities are given in the form of a diagram.

Firstly (step E1) an NEMS or MEMS sensor is produced including one or more cMUT transducers, as described above.

After this (step E2), the sensor suitable for the material to be studied is encapsulated.

Then (step E3) multiple sensors are dispersed in the material to be studied in liquid form, prior to its solidification.

Then (step E4) the sensors incorporated in the material are queried in order to produce a statistical reconstruction of the material's porosity.

The sensors are then queried (steps E5) several times during the lifetime of the material, in order to monitor changes to the microporosity.

According to a particular example application of a device according to the invention, sensors may be incorporated in a material such as plaster, in order for example to detect variations of humidity in this material.

An application to such a material may be useful notably in the construction field, or in the medical field, for example in order to detect haemorrhages under a plaster.

According to a possible implementation the sensors may be protected and encapsulated by at least one protective layer or coating.

With such a protective layer two types of protection may be implemented: protection during immersion of the sensors in the material to be studied, and protection during the sensor's lifetime.

A temporary protection, with a view to dispersing the sensors in the material to be studied may be applied, for example, using a thick packaging, which can degrade subsequently. Such a packaging may include, for example, one or more layers of polymers, for example linear polyesters of the PET type, able to be hydrolysed slowly in a basic medium. According to another example, such a packaging may have a photosensitive resin as its base.

A protection designed to last for the lifetime of the sensor may also be implemented. Such a protection may be formed from another polymer coating such as a polyester, for example one which resists a basic medium or, for example, parylene.

Figure 8:
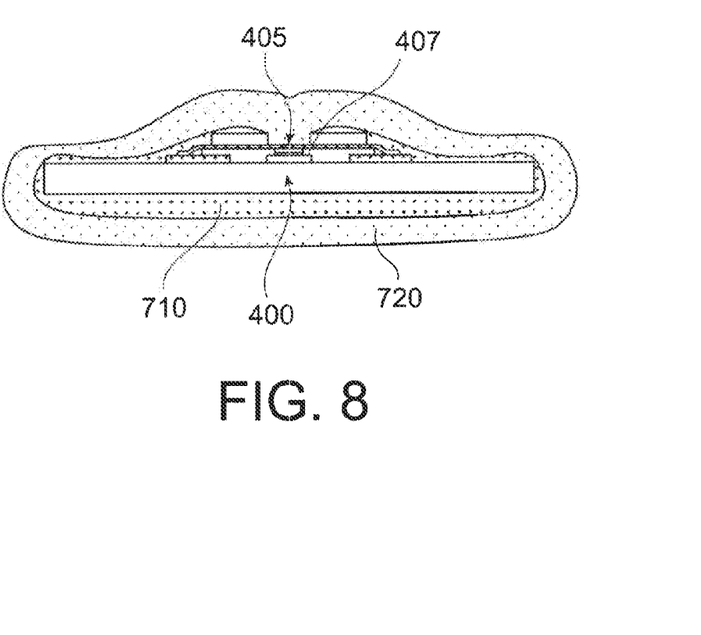
FIG. 8 illustrates a cMUT transducer designed for analysis of the microporosity of a material, and which is encapsulated in a protective casing formed from at least one temporary protective polymer layer covering another polymer layer intended to protect the cMUT transducer during its lifetime.

In FIG. 8 a cMUT sensor of a device according to the invention is represented with a protective casing encapsulating the sensor 100, where the casing is formed from a first protective layer 710, which may be designed to cover the entire sensor, or the entire sensor except for its active zone or active zones including, for example, one or more membranes and one or more cavities in which a membrane 405, or several membranes 405, are intended to vibrate.

The first protective layer 710 may be permanent and designed to protect the sensor for the duration of its lifetime. The first protective layer 710 may, for example, have a parylene base.

The first protective layer 710 may have as its base a material designed to resist chemical attack, particularly an acidic or basic medium.

For example, the first protective layer 710 may have as its base a stable material with a pH of the order of 12.

The chosen material may be a material which is compatible with a method of the same type as those used in microelectronics or microtechnologies.

The material may, for example, be parylene, which is chemically stable both in a basic and in an acidic medium, which may be used as a protection against humidity.

In the event (represented in this FIG. 8) that the sensitive zone or sensitive zones of the sensor are not protected by the first protective layer 710 the sensitive zones can then have been subjected to treatments to make them hydrophilic or hydrophobic (as described in the application filed by the Applicant numbered EN 08 57928).

To protect from chemical attacks certain parts of the sensor, close to or directly adjoining the sensitive zone or the sensitive zones, for example such as one or more actuation or detection electrodes 407, it is then also possible to encapsulate these parts permanently, using the same material as that of the first layer 710, or another material able to have the same properties of resistance to chemical attacks.

The first protective layer 710 may have a thickness for example of the order of one micron or of one tenth of a micron, in particular in the case in which the sensor is a cMUT sensor as described above.

The casing is also formed from a second protective layer 720, covering the first protective layer 710, and the active zone or active zones of the sensor.

The second protective layer 720 is temporary, and is designed to protect the sensor temporarily during its installation in a material to be studied. The second protective layer 720 may be intended to deteriorate after this installation.

The second protective layer 720 may have as its base a material designed to deteriorate gradually when the sensor is placed in a material to be analysed.

The second protective layer 720 may have as its base a material designed to deteriorate gradually, for example when it is placed in an acidic or basic medium.

The second temporary protective layer 720 of a material may be, for example, a temporary protective material which is soluble in an alkaline medium.

The second temporary protective layer 720 may thus have as its base, for example, a polymer material called an "alkaline-soluble" material, for example a material such as that described in the document: "*Surface properties of an associative alkali soluble polymer (Acrysol TT-935) Colloids and Surfaces A: Physicochemical and Engineering Aspects*", E. Hernández-Baltazar, G. A. Reyes-Sandoval, J. Gracia-Fadrique Volume 238, Issues 1-3, 4 May 2004, pages 113-122.

The second temporary protective layer 720 is designed to resist at least for a period required to incorporate the sensors in a material and to implement the measuring device.

The second temporary protective layer 720 is designed notably to protect the sensitive zone of the sensor from impacts due to movements of the various constituents of the material in which the sensors are incorporated, before this material sets permanently.

The temporary protective layer 720 is designed to be able to dissolve completely, and is therefore formed, in terms of material used, of thickness and possibly of the manner in which its surface has been treated, such that dissolution occurs principally during the first phases of solidification of the material to be analysed, and completes when the material containing the sensors is nearly completely set. In certain particularly fast-setting materials, this duration may be, for example, of around one hour. In the case of a cement material the duration generally exceeds 24 hours, and complete solidification may take several days.

The material chosen to produce the second temporary protective layer 720 may be a material which is compatible with a method of the same type as those used in microelectronics or microtechnologies.

This material may, for example, have as its base a photosensitive resin, such as a positive resin, and be formed from an alkaline-soluble polymer, such as for example DNQ-Novolac as described for example in the article: "*Synthesis of alkali-soluble silicone resin suitable for resist material in microlithography*", Hiroshi Ban, Akinobu Tanaka, Yoshio Kawai, Saburo Imamura, Polymer, Volume 31, Issue 3, March 1990, pages 564-568. It is also possible to use a negative photosensitive resin such as, for example, the resin SU-8®.

For temporary protection against alkaline media, in order to prevent an instantaneous dissolution of the resin, the composition of the resin is suited to the medium's degree of alkalinity.

The thickness of the second temporary protective layer 720 may be between, for example, 1 µm and 100 µm.

When a relatively thin protective layer 720, for example of a thickness of between 1 µm and 10 µm, is used, volume hardening, for example using a thermal treatment, and/or surface hardening, for example using an $O_2$ plasma, may be undertaken.

The temporary protective casing 720 may be rigidified. In particular, if it is necessary in the case of a flexible structure, for example a membrane, to prevent it being deformed and/or to prevent it adhering to the bottom of a cavity. It is possible, for example, to use gelatine to make the temporary protective casing 720 more rigid.

A method of rigidification using gelatine is presented, for example, in the article: *Photo-patternable gelatin as protection layers in low-temperature surface micromachinings*, Lung-Jieh Yang, Wei-Zhi Lin, Tze-Jung Yao, Yu-Chong Tai, Sensors and Actuators A: Physical, Volume 103, Issues 1-2, 15 Jan. 2003, Pages 284-290.

The invention claimed is:

1. A device for analyzing microporosities of a given material, that is porous and at least partially solidified the pores of which are smaller than 100 µm, wherein the material includes at least a solid phase and a gaseous phase or liquid phase, the device comprising:
multiple sensors introduced into the given material,
wherein each of said multiple sensors each include one or more capacitive micromachined ultrasonic transducers (cMUT) including one or more sensitive zones, the sensitive zones being configured to vibrate so as to emit and/or receive acoustic waves, and the critical dimension of each one of the one or more sensitive zones is between 1 nm and 100 μm.

2. A device according to claim 1, wherein each of said multiple sensors includes at least one cMUT receiver and multiple cMUT emitters incorporated in the given material, and configured to emit acoustic waves.

3. A device according to claim 2, wherein the cMUT emitters emit acoustic pulses in a range of frequencies of between 20 kHz and 100 MHz or between 100 MHz and 10 GHz.

4. A device according to claim 1, wherein the transducers include at least one membrane configured to oscillate, wherein the membrane has a length and a width each of which is less than 100 μm.

5. A device according to claim 1, wherein the transducers include at least one membrane configured to oscillate under effect of an electric field or an acoustic wave, wherein the membrane is formed from one or more layers of nanotubes, or nanowires, or nanorods.

6. A device according to claim 1, further comprising multiple supports of the multiple sensors incorporated in the given material, wherein each of the multiple sensors lies on at least one of said multiple supports, said at least one of said multiple supports including at least one electronic circuit to process signals produced by at least one of said multiple sensors.

7. A device according to claim 6, wherein each of said multiple supports of the sensors includes a matrix of sensors or plural sensors of different types.

8. A device according to claim 1, wherein the sensors include an integrated power source or are powered through a power source external to the material.

9. A device according to claim 1, wherein the sensors include means to emit signals to outside the material,
wherein the device further comprises a data-processing device which is external to the material, and which is connected to the sensors through RF or wired connections.

10. A device according to claim 1, wherein at least one sensor of said multiple sensors is protected by a protective casing formed from at least one permanent protective layer, which is stable in a basic or acidic medium.

11. A device according to claim 10, wherein the at least one sensor includes at least one sensitive zone configured to emit and/or receive acoustic waves, wherein the permanent protective layer partially covers the at least one sensor such that the at least one sensitive zone is not covered by the permanent protective layer.

12. A device according to claim 10, wherein the protective casing is formed from at least one other temporary protective layer, configured to deteriorate gradually after incorporation in the material.

13. A method for analysis of porosity of a given material including at least two phases, said given material being destined to change during its fabrication from a liquid state to at least a partially solidified state, when in the at least partially solidified state said given material including a solid phase and a liquid phase or a gaseous phase, or of a cement material, the method comprising:
    introducing one or more capacitive micromachined ultrasonic transducers (cMUT) of a device according to claim 1 in said given material during its liquid state, then after at least partial solidification of said given material,
    emission of at least one given acoustic wave by one or more capacitive micromachined ultrasonic transducers (cMUT) the one or more cMUTs being incorporated in the given material, and reception of at least one wave resulting from the emission of the given acoustic wave by at least one of said one or more cMUTs, wherein the at least one of said one or more cMUTs is incorporated in the given material.

14. A method according to claim 13, wherein prior to a measurement the multiple sensors are distributed at random in the given material when the given material is in an at least partially liquid state, and wherein the measurement is made after at least partial solidification of the given material.

15. A method according to claim 14, wherein, when the multiple sensors are distributed in the given material when the given material is in an at least partially liquid state, one or more of the multiple sensors are protected by a protective casing formed from at least one permanent protective layer, wherein the protective casing is formed from at least one other temporary protective layer, configured to deteriorate gradually after incorporation in the given material.

* * * * *